US00PP12161P2

(12) United States Plant Patent
Fuess

(10) Patent No.: US PP12,161 P2
(45) Date of Patent: Oct. 23, 2001

(54) CHRYSANTHEMUM PLANT NAMED 'EMPIRE SILHOUETTE'

(76) Inventor: Janet S. Fuess, 22 Country Club Dr., New York Mills, NY (US) 13417

( * ) Notice: Subject to any disclaimer, the term of this patent is extended or adjusted under 35 U.S.C. 154(b) by 0 days.

(21) Appl. No.: 09/475,973

(22) Filed: Dec. 31, 1999

(51) Int. Cl.[7] ..... A01H 5/00
(52) U.S. Cl. ..... Plt./287
(58) Field of Search ..... Plt./287, 291, 292

*Primary Examiner*—Howard J. Locker
(74) *Attorney, Agent, or Firm*—C. A. Whealy

(57) ABSTRACT

A distinct cultivar of Chrysanthemum plant named 'Empire Silhouette', characterized by its outwardly spreading and freely branching habit; decorative-type inflorescences that are about 4.5 to 5.5 cm in diameter; numerous attractive and unusual pink bi-colored ray florets; ray floret color that resists fading with development; compact cushion habit; numerous inflorescences per plant; early flowering response; and excellent garden performance.

1 Drawing Sheet

BACKGROUND OF THE INVENTION

The present invention relates to a new and distinct cultivar of Chrysanthemum plant, botanically known as *Dendranthema grandiflora* and referred to by the cultivar name Empire Silhouette.

The new cultivar is a product of a planned breeding program conducted by the Inventor in New Hartford, N.Y. The objective of the breeding program is to create new garden-type Chrysanthemum cultivars having inflorescences with desirable inflorescence forms, attractive floret colors and good garden performance.

The new cultivar originated from a cross made by the Inventor in *1996*, of the *Dendranthema grandiflora* cultivar Empire Eclipse, disclosed in U.S. Plant Pat. No. 11,093, as the female, or seed, parent with the *Dendranthema grandiflora* cultivar Empire Cabernet, disclosed in U.S. Plant Pat. No. 9,927.

The cultivar Empire Silhouette was discovered and selected by the Inventor as a flowering plant within the progeny of the stated cross in a controlled environment in New Hartford in September, 1997. The selection of this plant was based on its desirable inflorescence form and floret color and excellent garden performance.

Asexual reproduction of the new cultivar by terminal cuttings taken in a controlled environment in New Hartford since October, 1997, has shown that the unique features of this new Chrysanthemum are stable and reproduced true to type in successive generations.

BRIEF SUMMARY OF THE INVENTION

The cultivar Empire Silhouette has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Empire Silhouette'. These characteristics in combination distinguish 'Empire Silhouette' as a new and distinct cultivar:

1. Outwardly spreading and freely branching habit.
2. Decorative-type inflorescences that are about 4.5 to 5.5 cm in diameter.
3. Numerous attractive and unusual pink bi-colored inflorescences.
4. Compact cushion habit.
5. Numerous inflorescences per plant.
6. Early flowering response.
7. Excellent garden performance.

Plants of the new Chrysanthemum are most similar to plants of the female parent, the cultivar Empire Eclipse. Plants of the new Chrysanthemum have lighter pink and smaller inflorescences than plants of the cultivar Empire Eclipse. In addition, plants of the new Chrysanthemum flower about one week earlier under natural daylength conditions and about 1.5 weeks earlier under artificially-manipulated daylengths than plants of the cultivar Empire Eclipse.

Plants of the new Chrysanthemum differ from plants of the male parent, the cultivar Empire Cabernet, primarily in ray floret color.

BRIEF DESCRIPTION OF THE PHOTOGRAPH

The accompanying photograph illustrates the overall appearance of the new cultivar as true as it is reasonably possible to obtain in colored reproductions of this type. Colors in the photographs may differ slightly from the color values cited in the detailed botanical description which more accurately describe the actual colors of the new Chrysanthemum. The photograph comprises a top perspective view of a typical flowering plant of 'Empire Silhouette'.

DETAILED BOTANICAL DESCRIPTION

In the following description, color references are made to The Royal Horticultural Society Colour Chart except where general terms of ordinary dictionary significance are used. The following observations and measurements describe plants grown in 20-cm containers in New Hartford, N.Y., under outdoor natural season conditions which approximate those generally used in commercial garden Chrysanthemum production. Measurements and comparisons were determined on Sep. 15, 1999 about mid-day under 4,000 foot-candles of light in New Hartford, N.Y.

Botanical classification: *Dendranthema grandiflora* cultivar Empire Silhouette.

Commercial classification: Decorative-type garden chrysanthemum.

Parentage:

*Female or seed parent.*—*Dendranthema grandiflora* cultivar Empire Eclipse, disclosed in U.S. Plant Pat. No. 11,093.

*Male or pollen parent.*—*Dendranthema grandiflora* cultivar Empire Cabernet, disclosed in U.S. Plant Pat. No. 9,927.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Perennial herbaceous decorative-type garden Chrysanthemum. Inverted triangle. Outwardly spreading and mounding. Freely branching.

*Plant height.*—About 25 to 35 cm.

*Foliage description.*—Leaf arrangement: Alternate. Length: About 7 to 7.5 cm. Width: About 3.5 to 4 cm. Base: Attenuate. Margin: Five-lobed. Color: Mature foliage upper surface: 137B. Mature foliage lower surface: 138A.

Inflorescence description:

*Appearance.*—Decorative-type inflorescence form; fully double inflorescences without disc florets. Compact cushion habit. Inflorescences borne on terminals above foliage, arising from leaf axils. Ray florets arranged acropetally on a capitulum. One inflorescence per terminal with numerous inflorescences per plant.

*Flowering response.*—Under natural conditions, plants flower abot September 10th in New Hartford, N.Y. Plants exposed to artificially-manipulated day-lengths will flower about 7 weeks after start of long nyctoperiod treatments.

*Inflorescence diameter.*—About 4.5 to 5.5 cm.

*Ray florets.*—Length: About 2.2 cm. Width: About 8 mm. Number of ray florets per inflorescence: About 232. Color: Upper surface: When opening, 179C; mature florets, 65C. Color change gives a bi-colored effect to the inflorescence: 179C at the center of the inflorescence surrounded by 65C to the outer edge of the inflorescence. Lower surface: 69A.

*Disc florets.*—None observed.

*Reproductive organs.*—Androecium: None, no disc florets observed. Gynoecium: Present on both ray and disc florets. Style appearance: Bifurcate. Style length: About 4 mm.

*Seed.*—Seed production has not been observed.

Disease resistance: Resistance to known Chrysanthemum diseases has not been observed on plants grown under commercial production conditions.

It is claimed:

1. A new and distinct cultivar of Chrysanthemum plant named 'Empire Silhouette', as illustrated and described.

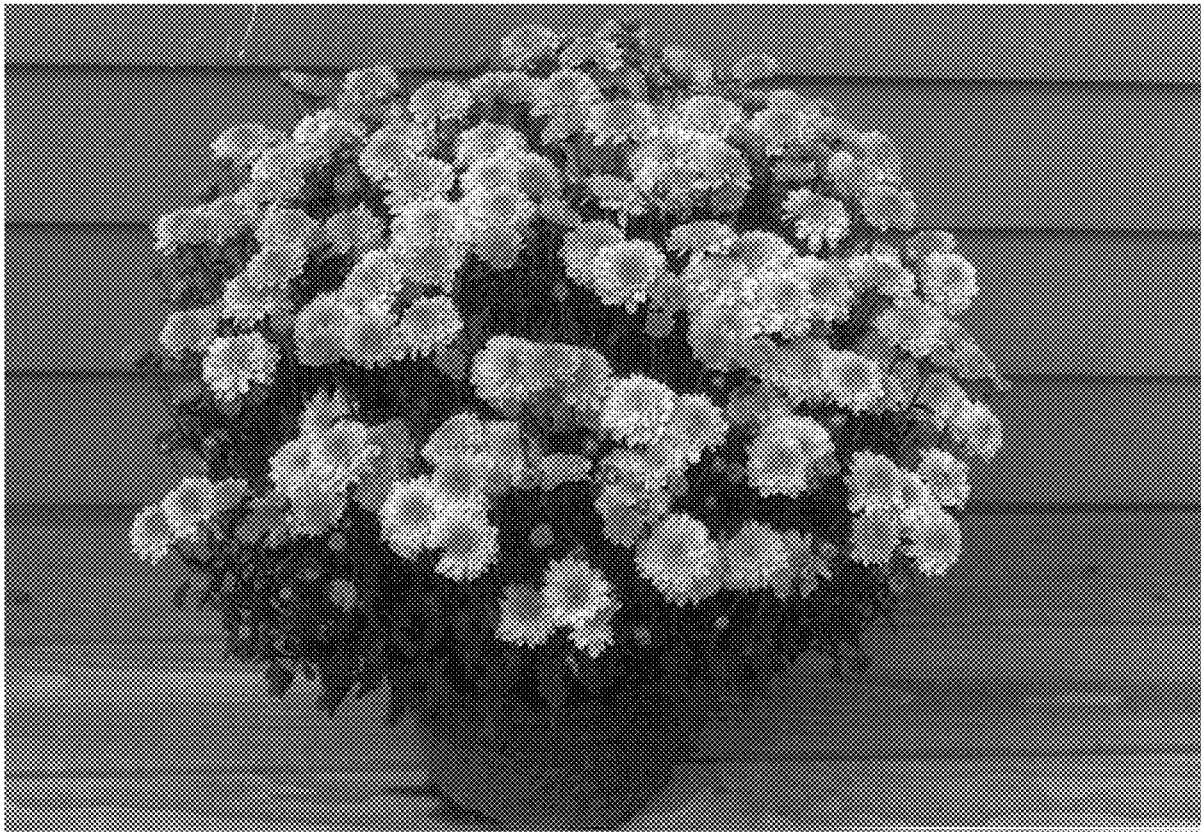

* * * * *